(12) United States Patent  (10) Patent No.: US 7,845,940 B2
Minium  (45) Date of Patent: *Dec. 7, 2010

(54) ORTHODONTIC APPARATUS WITH SELF-LIGATING BRACKET AND LOCKING DEVICE

(76) Inventor: Mark Minium, 1141 Dry Powder Cir., Mechanicsburg, PA (US) 17050

( * ) Notice: Subject to any disclaimer, the term of this patent is extended or adjusted under 35 U.S.C. 154(b) by 0 days.

This patent is subject to a terminal disclaimer.

(21) Appl. No.: 12/203,479

(22) Filed: Sep. 3, 2008

(65) Prior Publication Data

US 2009/0117510 A1 May 7, 2009

Related U.S. Application Data

(63) Continuation-in-part of application No. 12/072,062, filed on Feb. 25, 2008, which is a continuation-in-part of application No. 11/982,199, filed on Nov. 2, 2007, now Pat. No. 7,731,496, application No. 12/203,479, which is a continuation-in-part of application No. 12/214,218, filed on Jun. 18, 2008, now Pat. No. 7,740,475, and a continuation of application No. 12/072,062, filed on Feb. 25, 2008, which is a continuation-in-part of application No. 11/982,199, filed on Nov. 2, 2007, now Pat. No. 7,731,496.

(51) Int. Cl.
*A61C 7/30* (2006.01)
(52) U.S. Cl. .......................................... 433/16; 433/10
(58) Field of Classification Search ................ 433/8–17
See application file for complete search history.

(56) References Cited

U.S. PATENT DOCUMENTS

| | | | |
|---|---|---|---|
| 1,974,106 A | 9/1934 | Gardella | |
| 2,379,011 A | 6/1945 | Laskin | |
| 2,595,683 A | 5/1952 | Monte | |
| 2,634,728 A | 4/1953 | Dale | |
| 3,203,098 A | 8/1965 | Petraitis | |
| 3,218,712 A | 11/1965 | Wallshein | |
| 3,291,476 A | 12/1966 | Calkin | |
| 3,421,221 A | 1/1969 | Silverman et al. | |
| 3,423,833 A | 1/1969 | Pearlman | |
| 3,461,559 A | 8/1969 | Silverman et al. | |
| 3,464,113 A | 9/1969 | Silverman et al. | |
| 3,721,005 A | 3/1973 | Cohen | |
| 3,871,098 A | 3/1975 | Dean | |
| 3,946,488 A | 3/1976 | Miller et al. | |
| 4,001,940 A | 1/1977 | Cusato | |
| 4,035,919 A | 7/1977 | Cusato | |
| 4,139,945 A | 2/1979 | DiGiulio | |
| 4,161,066 A | 7/1979 | Morrow et al. | |
| 4,243,387 A | 1/1981 | Prins | |
| 4,353,692 A | 10/1982 | Karrakussoglu | |
| 4,487,580 A | 12/1984 | Ridgeway | |
| 4,487,581 A | 12/1984 | Adler | |
| 4,597,739 A | 7/1986 | Rosenberg | |
| 4,676,746 A | 6/1987 | Klapper | |
| 4,712,999 A * | 12/1987 | Rosenberg | 433/8 |

(Continued)

*Primary Examiner*—Cris L Rodriguez
*Assistant Examiner*—Michael R Ballinger

(57) ABSTRACT

An orthodontic bracket system is provided having a base plate with a rear side and a front side. The rear side is designed to engage a patient's tooth. The front side includes a channel for receiving an archwire, a cover plate for closing the opening of the channel and securing the archwire within the channel, and a locking device designed to engage the cover plate during a closed position.

21 Claims, 18 Drawing Sheets

U.S. PATENT DOCUMENTS

| | | | |
|---|---|---|---|
| 4,786,252 A | 11/1988 | Fujita | |
| 4,867,678 A | 9/1989 | Parker | |
| 4,917,602 A | 4/1990 | Broussard | |
| 5,094,614 A | 3/1992 | Wildman | |
| 5,474,445 A * | 12/1995 | Voudouris | 433/10 |
| 5,520,704 A | 5/1996 | Castro et al. | |
| 5,711,666 A | 1/1998 | Hanson | |
| 5,738,513 A * | 4/1998 | Hermann | 433/13 |
| 5,857,850 A * | 1/1999 | Voudouris | 433/11 |
| 5,868,787 A | 2/1999 | Kim | |
| 5,906,486 A | 5/1999 | Hanson | |
| 5,908,293 A * | 6/1999 | Voudouris | 433/10 |
| 5,954,502 A | 9/1999 | Tuenge et al. | |
| 6,042,373 A * | 3/2000 | Hermann | 433/13 |
| 6,190,166 B1 | 2/2001 | Sasakura | |
| 6,447,291 B2 | 9/2002 | Kim | |
| 6,733,286 B2 | 5/2004 | Abels et al. | |
| 6,786,719 B2 | 9/2004 | McGann | |
| 6,939,133 B2 * | 9/2005 | Voudouris | 433/11 |
| 7,104,791 B2 | 9/2006 | Hanson | |
| 7,267,545 B2 | 9/2007 | Oda | |
| 7,431,586 B1 * | 10/2008 | Silverman | 433/9 |
| 2004/0072117 A1 | 4/2004 | Farzin-Nia et al. | |
| 2004/0166458 A1 * | 8/2004 | Opin et al. | 433/11 |
| 2006/0008761 A1 | 1/2006 | Allred | |
| 2006/0154196 A1 | 7/2006 | Oda | |
| 2006/0263737 A1 | 11/2006 | Oda | |
| 2006/0269889 A1 * | 11/2006 | Voudouris | 433/11 |
| 2007/0092849 A1 * | 4/2007 | Cosse | 433/8 |
| 2007/0224569 A1 | 9/2007 | Oda | |

\* cited by examiner

ORTHODONTIC APPARATUS WITH SELF-LIGATING BRACKET AND LOCKING DEVICE

CROSS REFERENCE TO RELATED APPLICATIONS

This application is a continuation-in-part of U.S. application Ser. No. 12/072,062, entitled "Orthodontic Apparatus With Self-Ligating Bracket", filed on Feb. 25, 2008, which is a continuation-in-part of U.S. application Ser. No. 11/982,199 entitled "Adjustable Orthodontic Apparatus", filed on Nov. 2, 2007; and a continuation-in-part of U.S. application Ser. No. 12/214,218, entitled "Orthodontic Apparatus With Adjustable Base Plate And Connecting Plate", filed on Jun. 18, 2008, which is a continuation-in-part of U.S. application Ser. No. 11/982,199 entitled "Adjustable Orthodontic Apparatus", filed on Nov. 2, 2007 and a continuation of U.S. application Ser. No. 12/072,062, entitled "Orthodontic Apparatus With Self-Ligating Bracket", filed on Feb. 25, 2008; and a continuation-in-part of U.S. application Ser. No. 11/982,199 entitled "Adjustable Orthodontic Apparatus", filed on Nov. 2, 2007; all incorporated by reference herein.

FIELD OF THE INVENTION

This invention relates to an orthodontic treatment apparatus and in particular, to a self-ligating orthodontic bracket.

BACKGROUND OF THE INVENTION

The science of orthodontics has been advancing at a rapid pace. Stainless steel wires traditionally used to apply orthodontic forces to teeth have in large part been replaced by high-tech alloy wires. These more flexible "memory" archwires employ the use of titanium, niobium, copper and other more efficient materials. Heat activated, these wires allow for lower, longer acting forces with more allowable deflection of the wire to engage brackets adhered to malpositioned teeth. Once engaged, the archwires are maintained within the brackets using steel ligatures, elastomeric ties, and most recently, self-ligating brackets of various designs.

Bracket placement has always been important in orthodontic therapy; the introduction of the self-ligating bracket has increased its importance. Because bracket position directly effects the force application of the archwire on, and ultimately the final position of, the tooth, proper bracket placement during treatment is critical. To aid in the positioning of the bracket at a tooth location which will bring the teeth to a desired physiologic final dental arch form, positioning instruments have been developed, indirect bonding has been used, and most recently, computer aided indirect bonding has been introduced.

Even using the newest and most advanced types of orthodontic brackets, a treatment visit is still required at about 6 months after the initial application of the brackets in order to refine bracket position to better achieve desired physiologic parallel root form. Using radiographic images for root repositioning guidance, this treatment visit is scheduled for all patients and often needs to be to be repeated during the treatment course, resulting in multiple time consuming bracket repositioning visits.

Sliding, reduced friction mechanics, the basis of modern orthodontic therapy, relies on using high-tech memory wires without bends. Because the metallurgic properties of modern high tech wires do not permit bending of these wires to compensate for less than ideal bracket placement, final tooth position is dependent upon ideal bracket placement. Therefore, during the course of treatment, additional time consuming bracket repositioning visits must be scheduled for those teeth that could not accommodate initial ideal bracket placement, further adding both time and expense to orthodontic treatment.

Accordingly, there is still a continuing need for improved orthodontic bracket designs. The present invention fulfills this need and further provides related advantages.

BRIEF SUMMARY OF THE INVENTION

To overcome these bracket repositioning problems, the present invention provides for a design that allows the bracket to be repositioned on a base without having to remove and re-adhere the base to the tooth. The novel design creates a repositionable interface between a bracket archwire slot and the base and can be used on any bracket design, for example, a standard style design requiring separate wire ligation or a self ligating design.

The novel apparatus of the present invention is strong, simple to use and allows for multiple options in bracket positioning, both vertically and horizontally. Application of this novel apparatus will reduce the need to reposition brackets by, for example, recementing or rebonding, and will reduce or eliminate the need to place compensating bends when traditional (stainless steel) archwires are used. The present invention will also reduce treatment time requirements as well as increase treatment efficiency, enabling patients to complete treatment in less time.

In a first embodiment, the invention comprises a bracket housing having at least two opposing sides, a rear side which is a tooth engaging side and a front side having a cavity for receiving at least one wire and a locking cover plate pivotally attached to the front side of the bracket housing. The cover plate is designed to be moveable from an open to a locked closed position to secure and hold the wire within the cavity of the front side of the bracket housing.

In a second embodiment, the present invention provides for an orthodontic bracket system comprising a base plate having a rear side and a front side, the rear side designed to engage a patient's tooth. The base plate further comprises a channel for receiving an archwire, the channel leading to an opening on the front side of the base plate; a cover plate for closing the opening of the channel and securing the archwire within the channel of the base plate; and an element for locking the cover plate in the closed position.

In another embodiment, the present invention provides for an adjustable orthodontic apparatus with a self ligating bracket. The apparatus comprises a base plate comprising opposing sides, a first side being a tooth engaging side and a second side for engaging and adjusting the vertical and horizontal position of a connecting plate. The connecting plate has opposing sides; a first side for engaging the second side of the base plate and allowing for the vertical and horizontal movement of the connecting plate as it relates to the base plate, and a second side having an archwire channel for receiving an archwire. A securing device locks the connecting plate to a desired position onto the base plate and a cover plate closes the opening of the archwire channel to secure the archwire within the channel of the base plate. A locking element locks the cover plate in a closed position.

Other features and advantages of the present invention will be apparent from the following more detailed description of the preferred embodiments, taken in conjunction with the accompanying drawings which illustrate, by way of example, the principles of the invention.

BRIEF DESCRIPTION OF THE DRAWINGS

The accompanying drawings are included to provide a further understanding of the present invention. These drawings are incorporated in and constitute a part of this specification, illustrate one or more embodiments of the present invention, and together with the description, serve to explain the principles of the present invention.

Among those benefits and improvements that have been disclosed, other objects and advantages of this invention will become apparent from the following description taken in conjunction with the accompanying drawings. The drawings constitute a part of this specification and include exemplary embodiments of the present invention and illustrate various objects and features thereof.

DETAILED DESCRIPTION OF THE INVENTION

As required, detailed embodiments of the present invention are disclosed herein; however, it is to be understood that the disclosed embodiments are merely exemplary of the invention that may be embodied in various forms. The figures are not necessary to scale, and some features may be exaggerated to show details of particular components. Therefore, specific structural and functional details disclosed herein are not to be interpreted as limiting, but merely as a basis for the claims and as a representative basis for teaching one skilled in the art to variously employ the present invention.

For purposes of this invention, a bracket is defined as any device which is fixed to the surface of a tooth and designed for attachment of archwires or auxiliaries such as for example, springs or elastics; used to transmit forces from these archwires and/or auxiliaries to the tooth and its supporting structures.

In most cases, tooth moving forces are stored in the archwire and/or auxiliaries and delivered through a bracket to the tooth and supporting structures by deflection of the archwire or auxiliary from a passive to an active state.

Traditionally, a bracket comprises a base; one or more archwire slots designed for receiving an archwire; and occlusal and gingival flanges or wings designed to receive elastic or metal ligatures used to maintain the archwire within the slot. The bracket is affixed to a tooth by direct bonding through the use of a mesh pad incorporated into the back of the bracket or the bracket is welded or brazed to a band which is cemented around the tooth. Newer, self ligating bracket designs incorporate, for example, a sliding door that closes over the slot, thereby holding the wire in place and obviating the need for separate ligatures.

Figure 1:
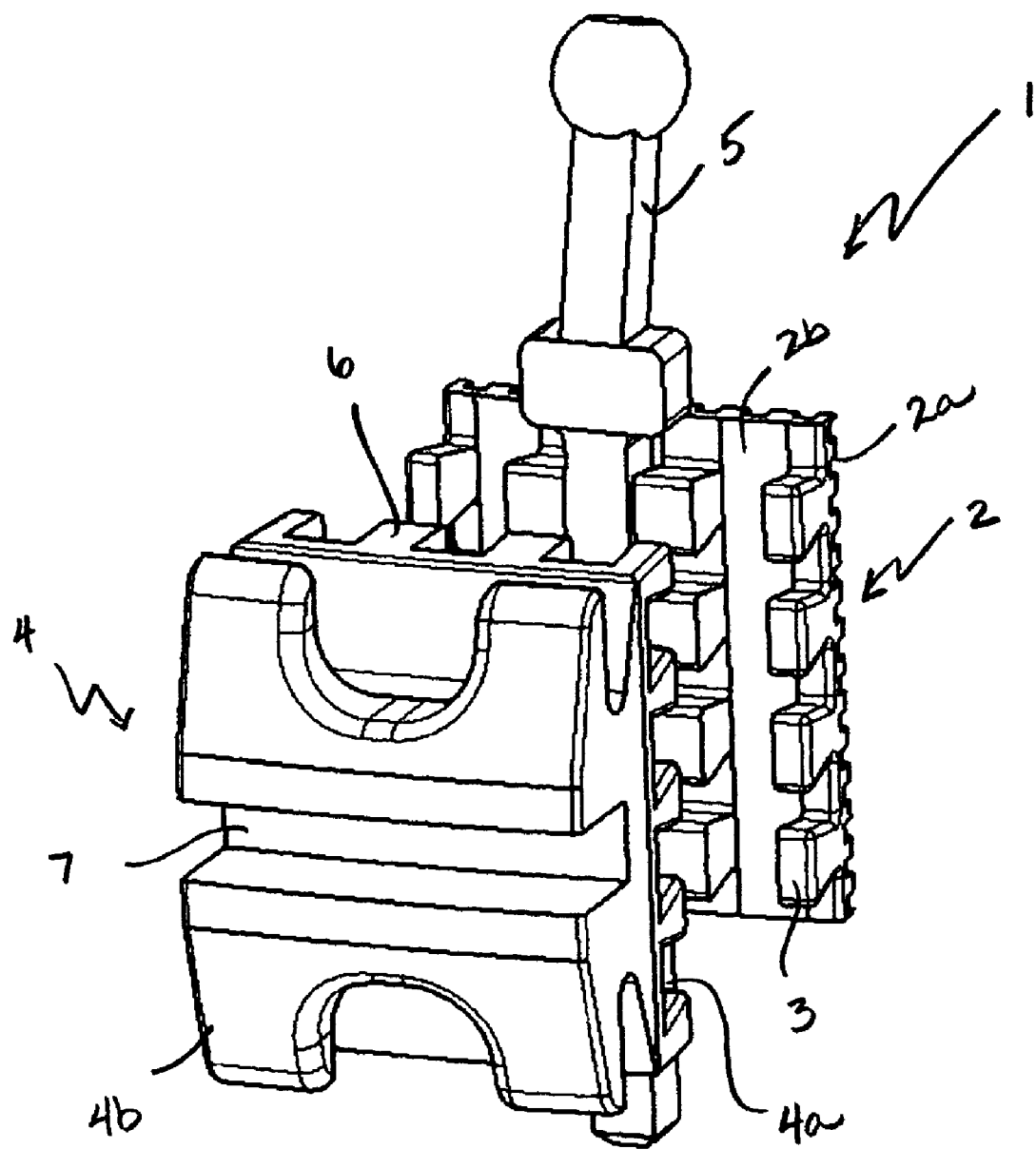
FIG. 1 is an exploded view of one of the embodiments of the present invention.
Figure 2:
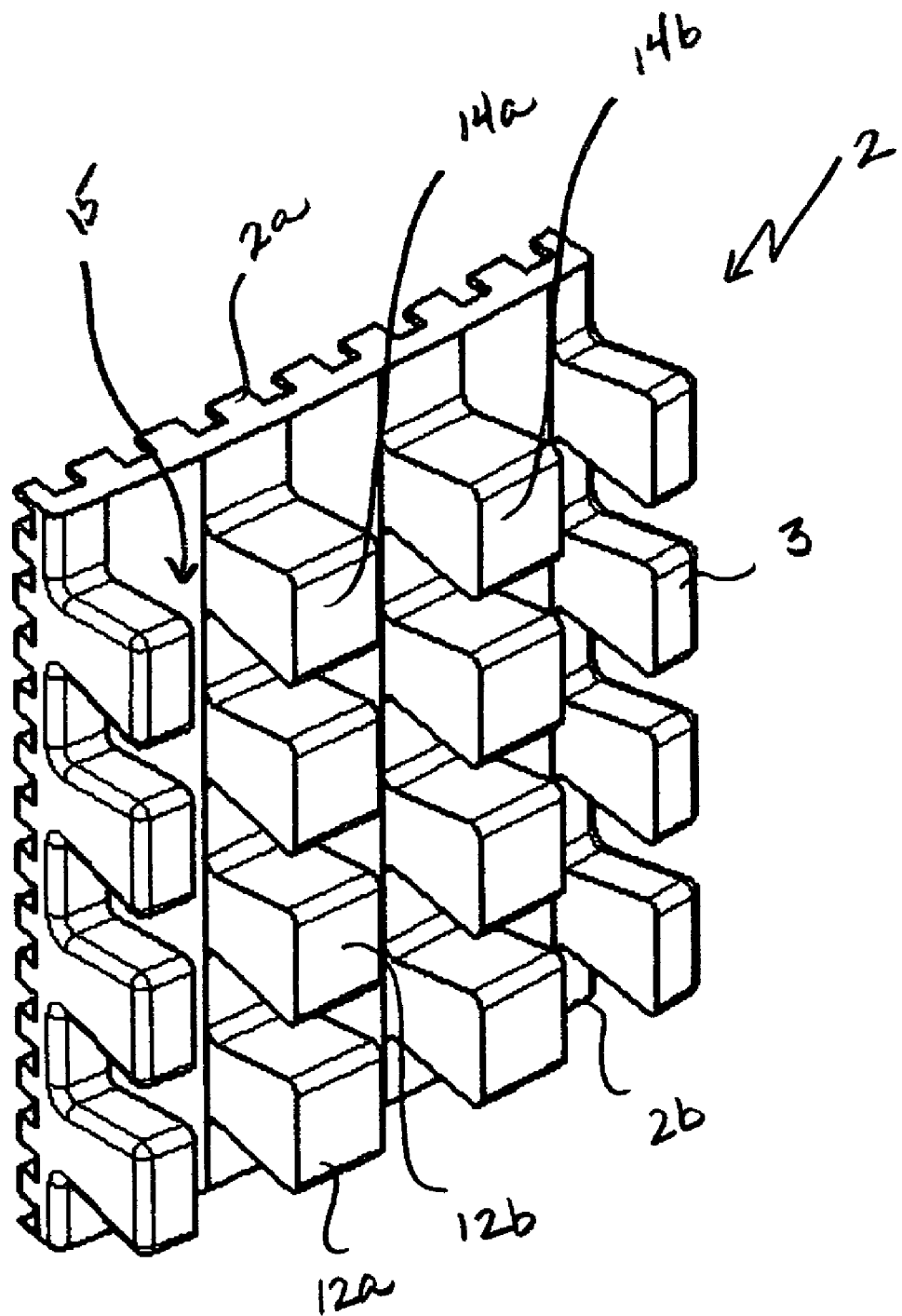
FIG. 2 is a front perspective view of one of the embodiments of the base plate of the present invention.
Figure 3:
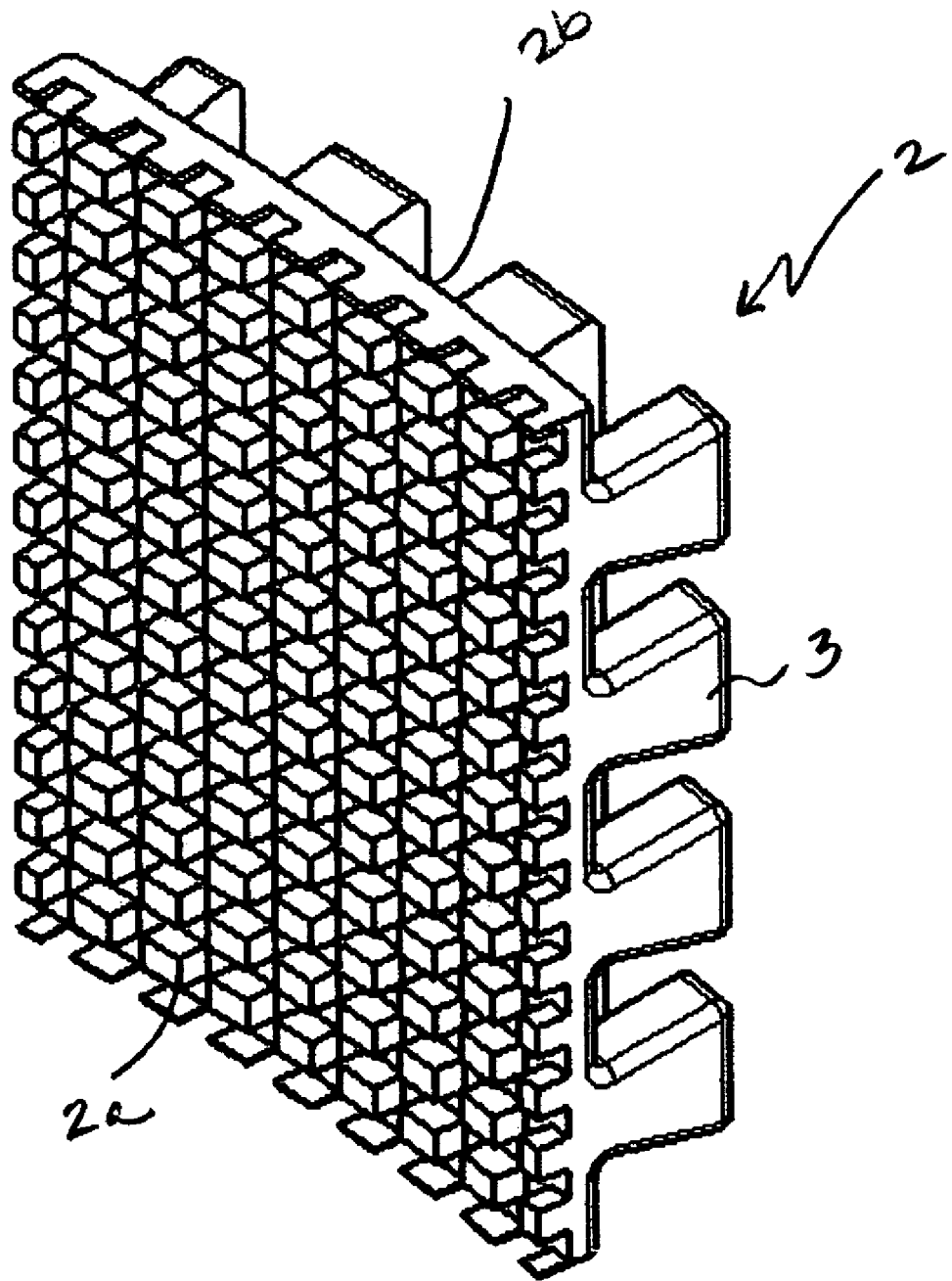
FIG. 3 is a back perspective view of the base plate in FIG. 2.
Figure 4:
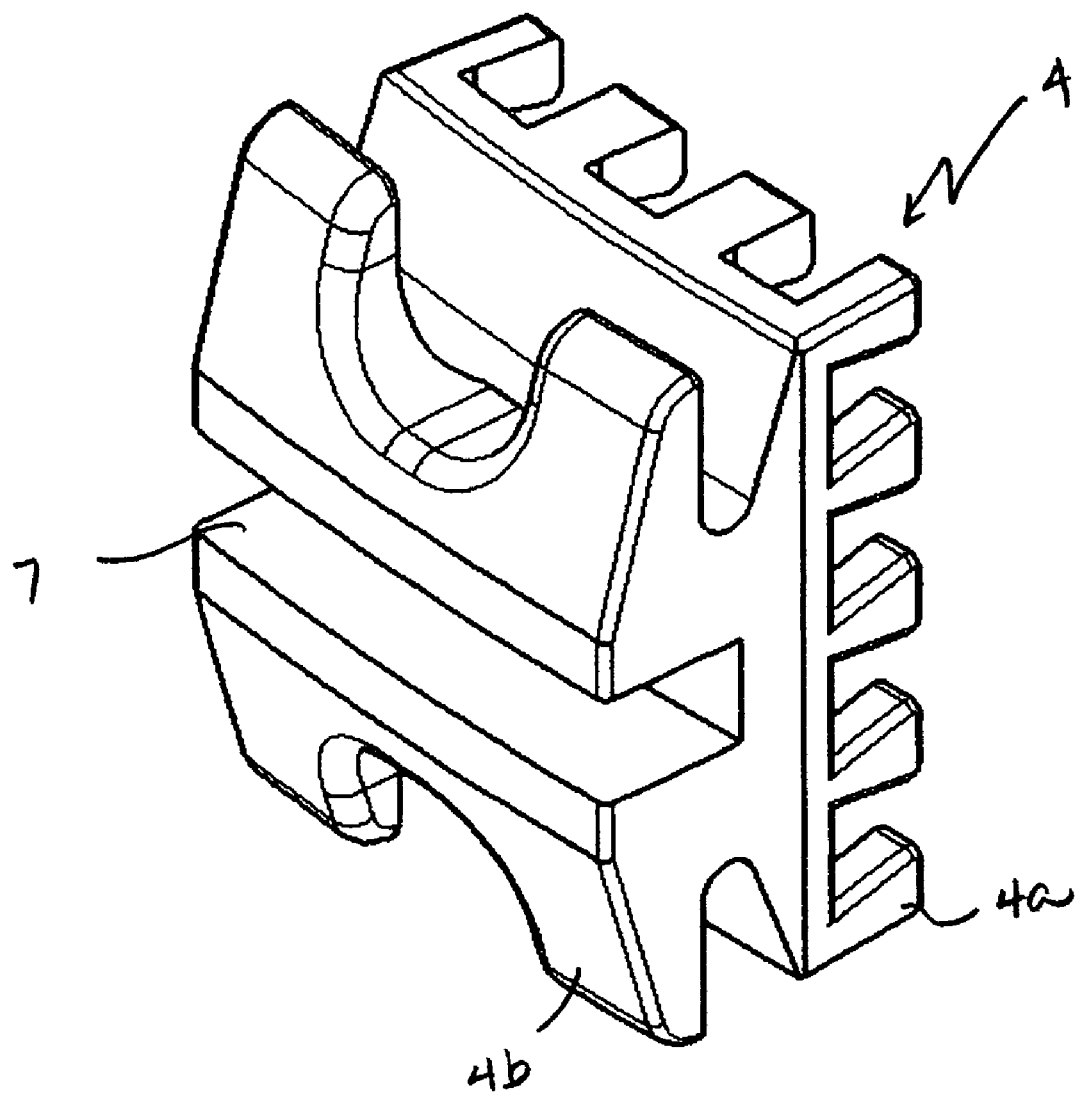
FIG. 4 is a frontal perspective view of one of the embodiments of the connecting plate of the present invention.
Figure 5:
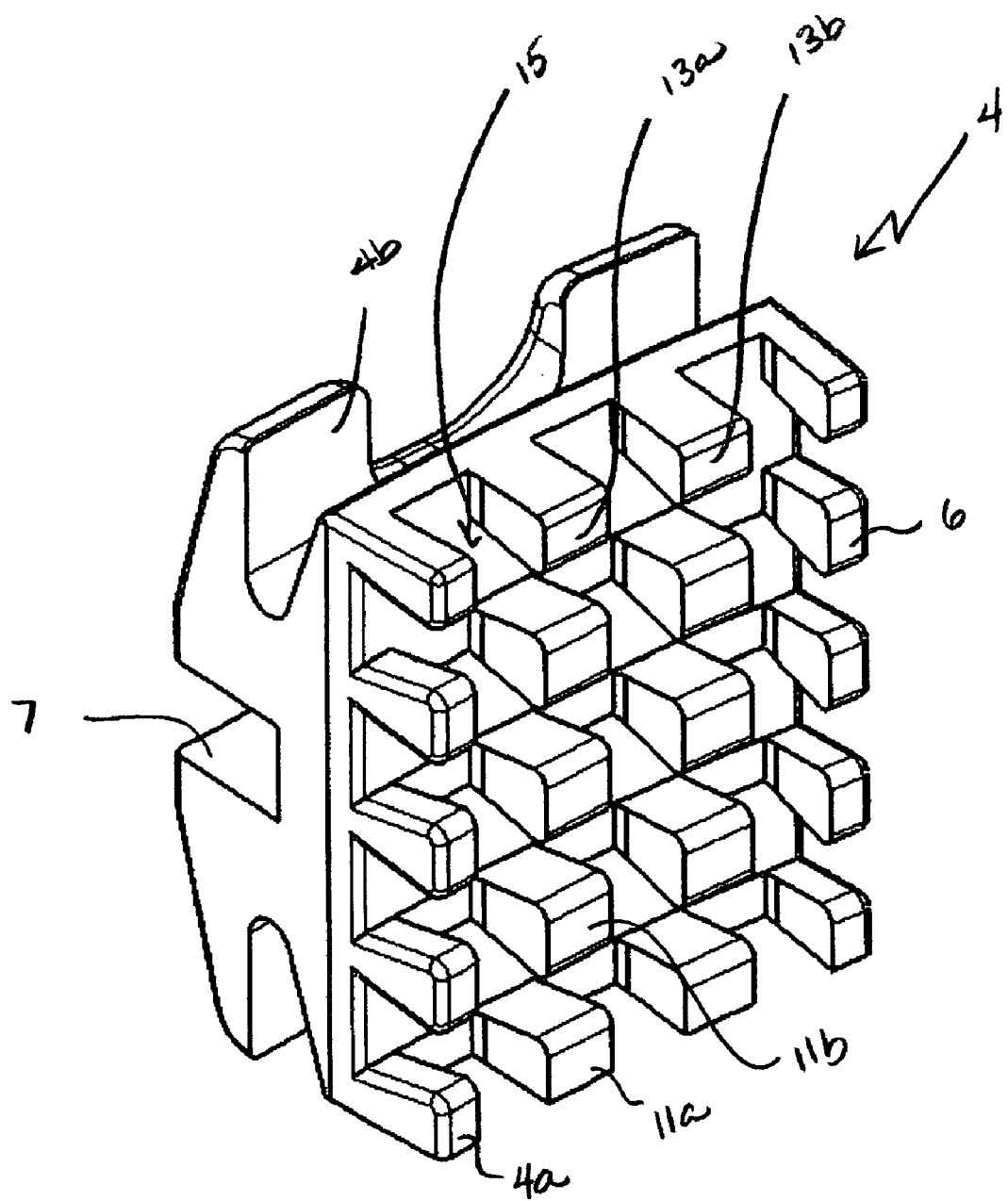
FIG. 5 is a back perspective view of the connecting plate in FIG. 4.

Turning now to the figures, FIG. 1 illustrates one of the embodiments of the present invention. More specifically, an adjustable orthodontic apparatus 1 is provided. The apparatus 1 comprises a base plate 2 comprising opposing sides, 2a and 2b respectively, a first side 2a being a tooth engaging side and a second side 2b comprises a first device 3 for engaging and adjusting the vertical and horizontal position of a connecting plate 4. The connecting plate 4 has opposing sides, 4a and 4b respectively, a first side 4a comprises a second device 6 for engaging the second side 2b of the base plate 2 and allowing for the vertical and horizontal movement of the connecting plate 4 as it relates to the base plate 2. The apparatus 1 further comprises a securing device 5 for locking the connecting plate 3 to a desired position onto the base plate 2.

The securing device 5 for locking the base plate 2 to the connecting plate 3 comprises, for example, a pin. The second side 4b of the connecting plate 4 comprises an orthodontic device 7. The orthodontic device 7 may be, for example, an archwire receiving bracket or an archwire receiving eyelet.

FIGS. 2-5 relate to the front and back views of the base plate 2 and connecting plate 4 of the present invention. The first device 3 of the second side 2b of the base plate 2 comprises at least two vertically positioned protrusions, 12a and 12b respectively, and at least two horizontally positioned protrusions, 14a and 14b respectively, and the second device 6 of the first side 4a of the connecting plate 4 comprises at least two vertically positioned protrusions, 11a and 11b respectively, and at least two horizontally positioned protrusions, 13a and 13b respectively.

There are a plurality of spaces in between each of the protrusions, 11a, 11b, 12a, 12b, 13a, 13b, 14a and 14b respectively, in the second side 2b of the base plate 2 and the first side 4a of the connecting plate 4. The plurality of spaces provides for channels 15 for protrusions, 11a, 11b, 12a, 12b, 13a, 13b, 14a and 14b respectively, to move during adjustment of the connecting plate 4 relative to the base plate 2 (described in greater detail below) and the securing device 5 is situated within the channel 15 when the connecting plate 4 is locked onto the base plate 2.

Figure 6:
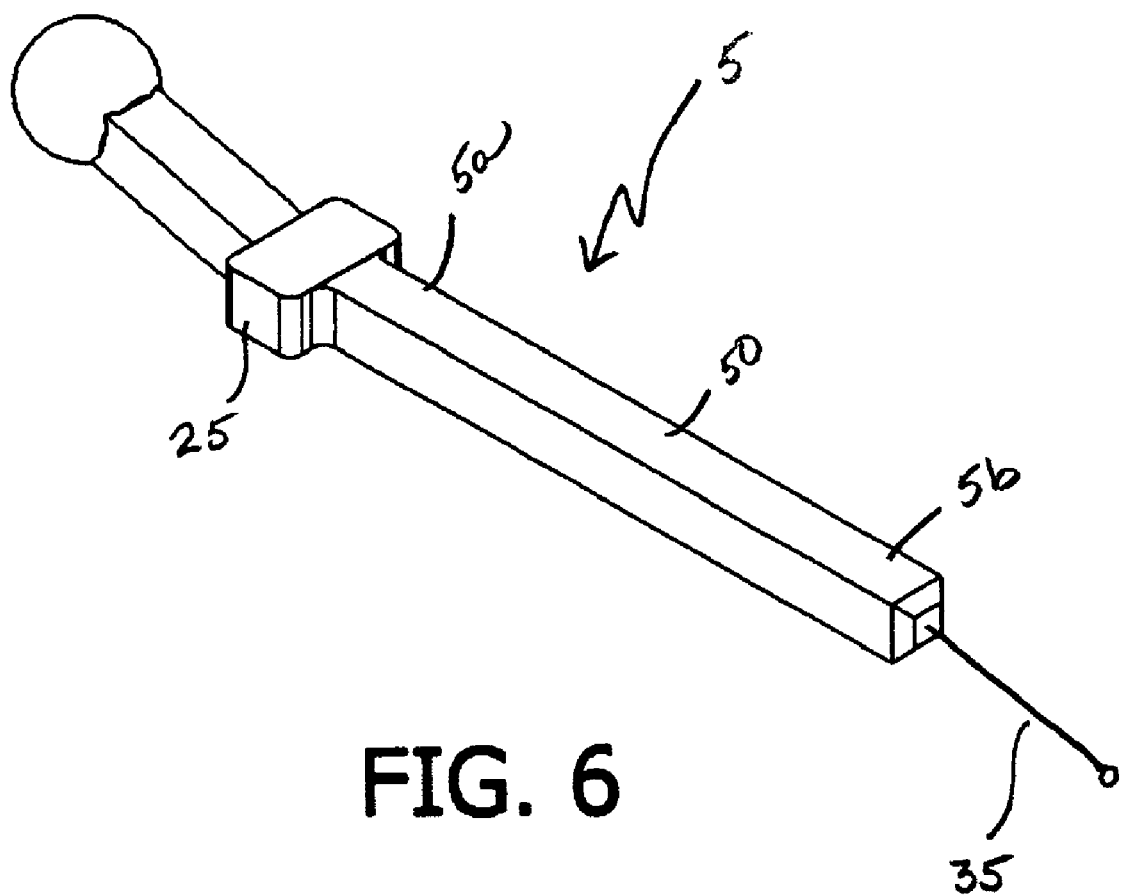
FIG. 6 is a perspective view of the securing device of the present invention.

FIG. 6 illustrates the securing device 5 which comprises an elongated shaft 50 designed to fit within the channels between the protrusions and also has opposing ends, 5a and 5b respectively. One side 5a has extended stop portion 25 and the opposing side 5b has a bendable portion 35 designed to lock the position of the connecting plate to the base plate. In another embodiment, side 5a is slightly bent at an angle.

Figure 7:
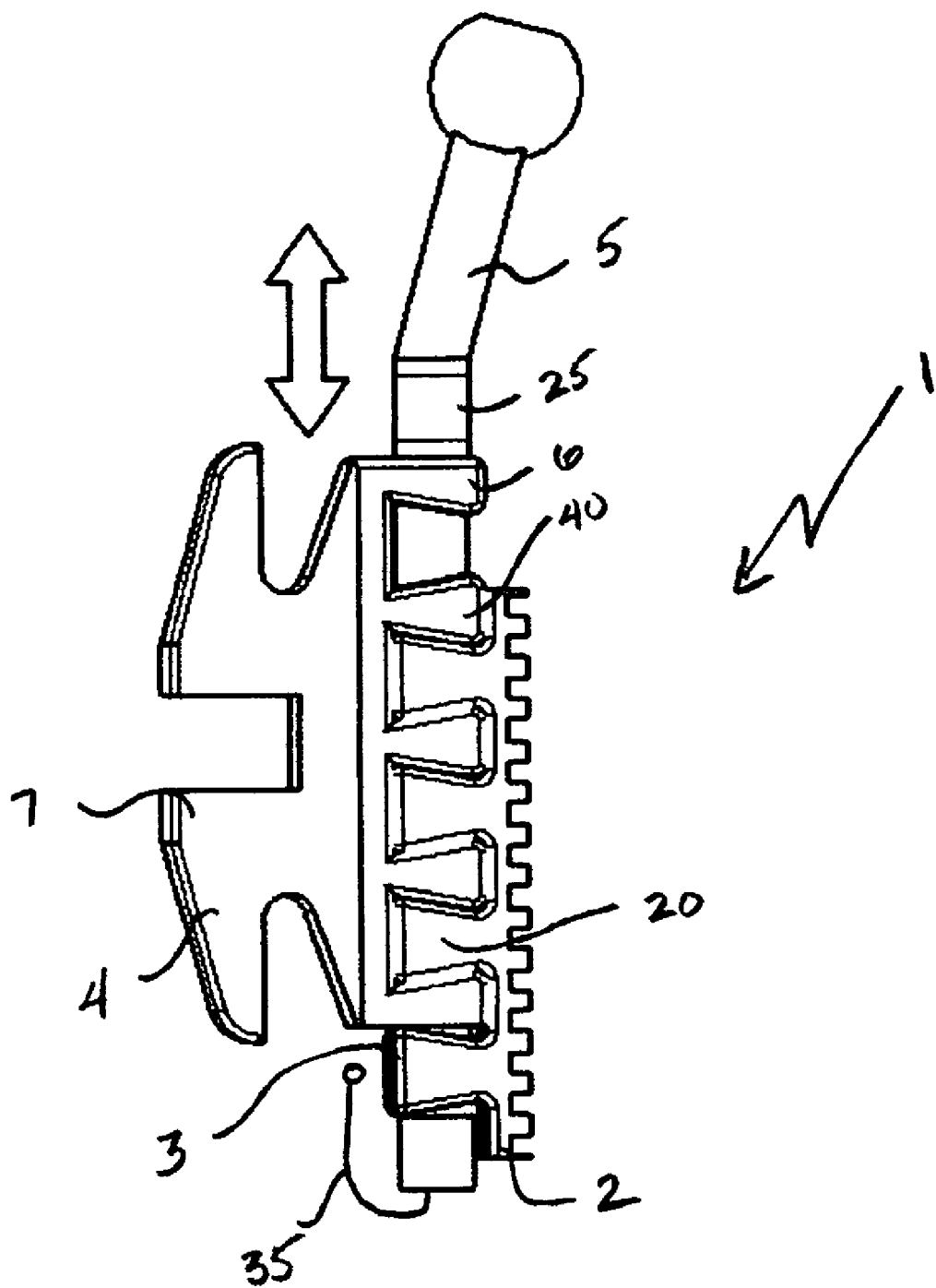
FIG. 7 is a side perspective view of the interaction of the connecting plate and the base plate of the present invention.
Figure 8:
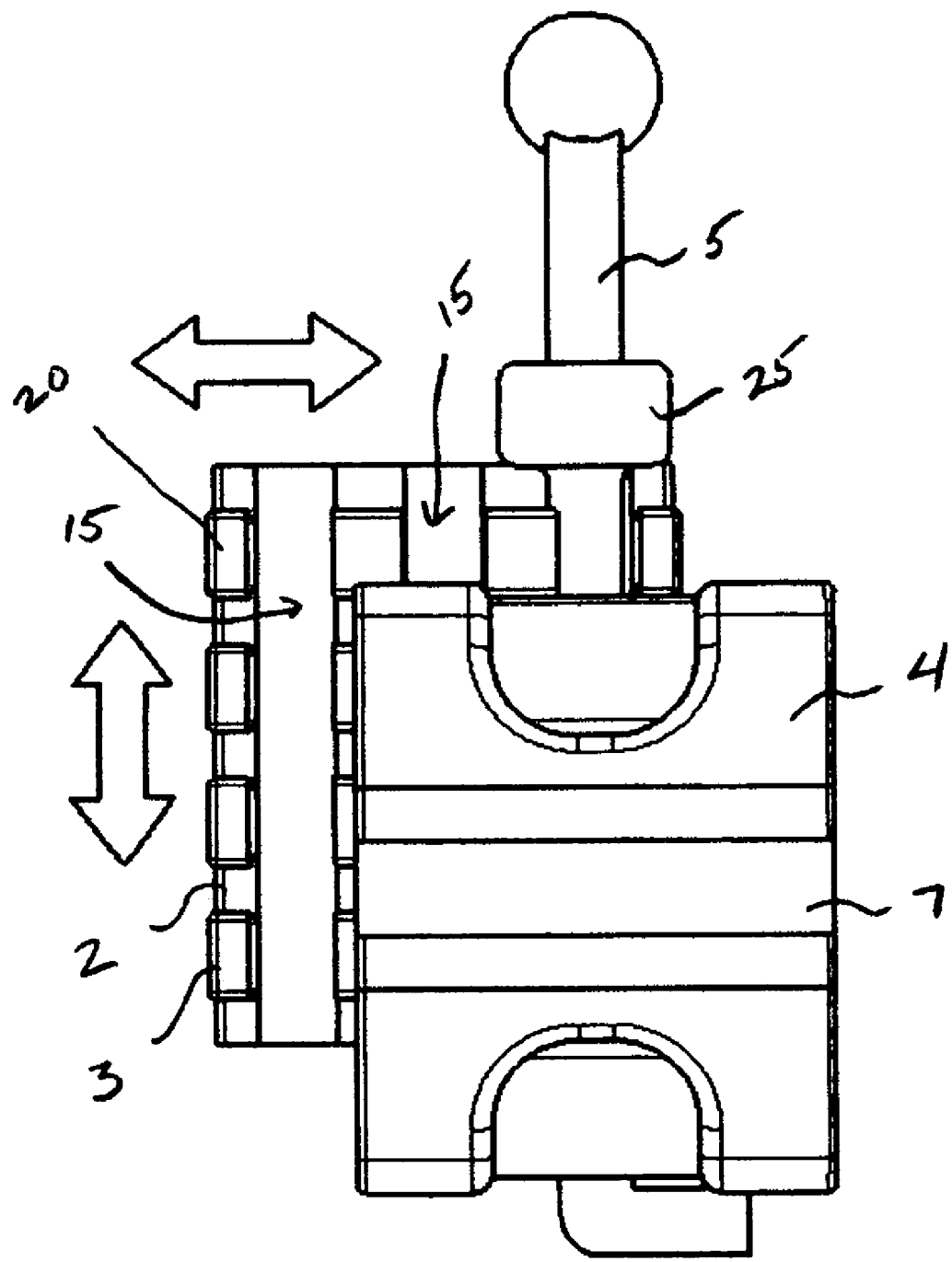
FIG. 8 is a frontal view of FIG. 7 showing the relationship and movement of the connecting plate relative to the base plate.

In another embodiment and as shown in FIGS. 7-8, the first device 3 of the second side 2b of the base plate 2 comprises a plurality of vertical and horizontal column of protrusions 20 and the second device 6 of the first side 4a of the connecting plate 4 comprises a plurality of vertical and horizontal column of protrusions 40, and the plurality of column of protrusions, 20 and 40 provides for a plurality of vertical and horizontal channels 15. The channels 15 provides the protrusion 20 and 40 to move during adjustment of the connecting plate 4 relative to the base plate 2 and the securing device 5 is situated with the channel 15 when the connecting plate 4 is locked into a certain position relative to the base plate 2. The protrusions 20 and 40 are designed to move vertically and horizontally within the channels 15 during the adjustment of the connecting plate 4 relative to the base plate 2. At least one of the protrusions 40 of the connecting plate 4 and at least one of the protrusions 20 of the base plate 2 engage one another when the securing device 5 locks the connecting plate 4 to the base plate 2.

The protrusions 20 and 40 of the base plate 2 and the connecting plate have geometric shapes, and at least one of the protrusions 20 of the base plate 2 has a geometric shape that creates a retentive undercut with the opposing geometric shape of at least one of the protrusions 40 of the connecting plate 4.

Figure 9:
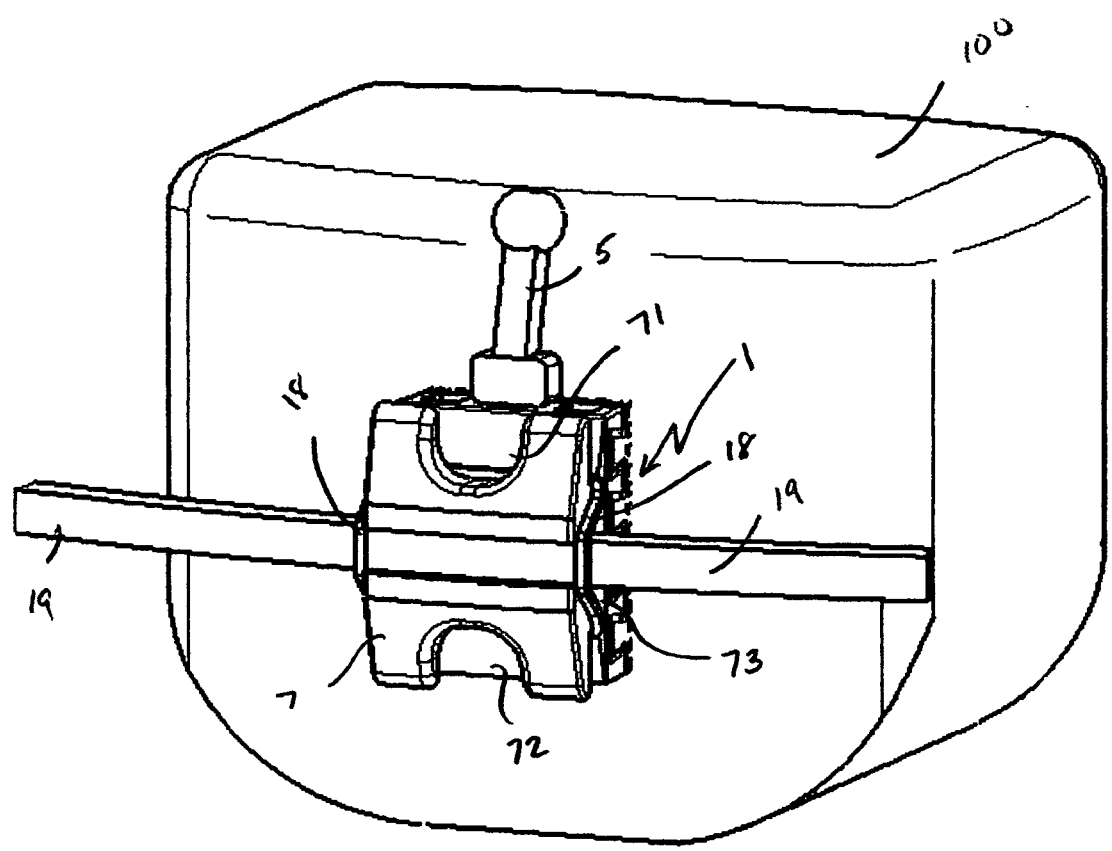
FIG. 9 is a perspective view of the orthodontic system of the present invention fully assembled on a patient's tooth.

FIG. 9 shows the orthodontic system 10 of the present invention assembled onto the tooth 100 of a patient. The tooth engaging side 2a of the base plate 2 is generally concave to conform with the curvature of a tooth 100. The orthodontic device 7 comprises at least two u-shaped protrusions, 71 and 72 respectively, on opposing ends 7a and 7b respectively; and a central cavity 73 for receiving a wire 19. At least one rubber band or steel ligature 18 is used to secure the wire 19 to the orthodontic device 7 within the cavity 73. The orthodontic device 7 is attached to the connecting plate 4 which is secured to the base plate 2 with the pin 5.

Figure 10:
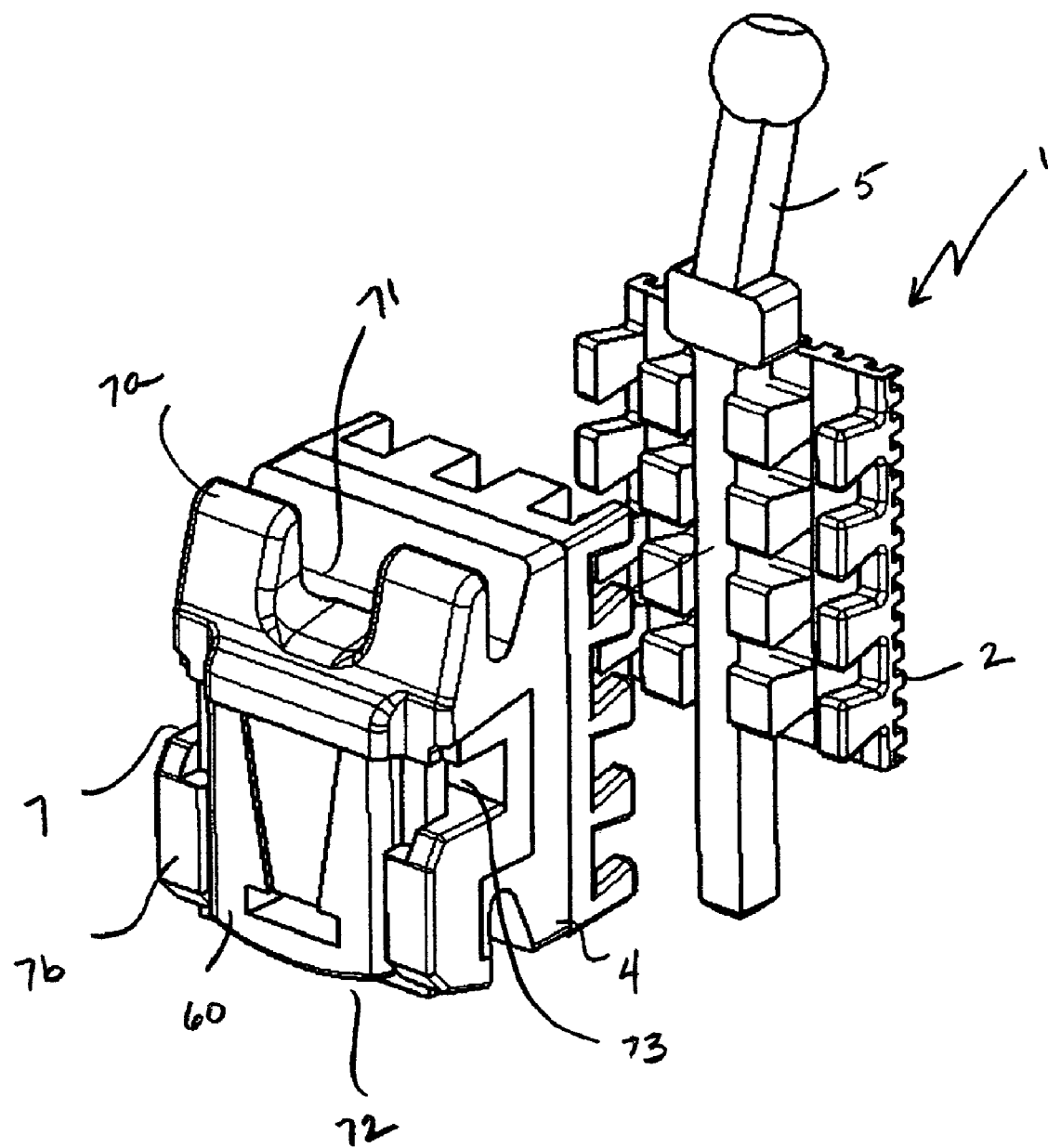
FIG. 10 depicts an exploded view of another embodiment of the orthodontic apparatus of the present invention with a connecting plate that has an opening and closing door.
Figure 11:
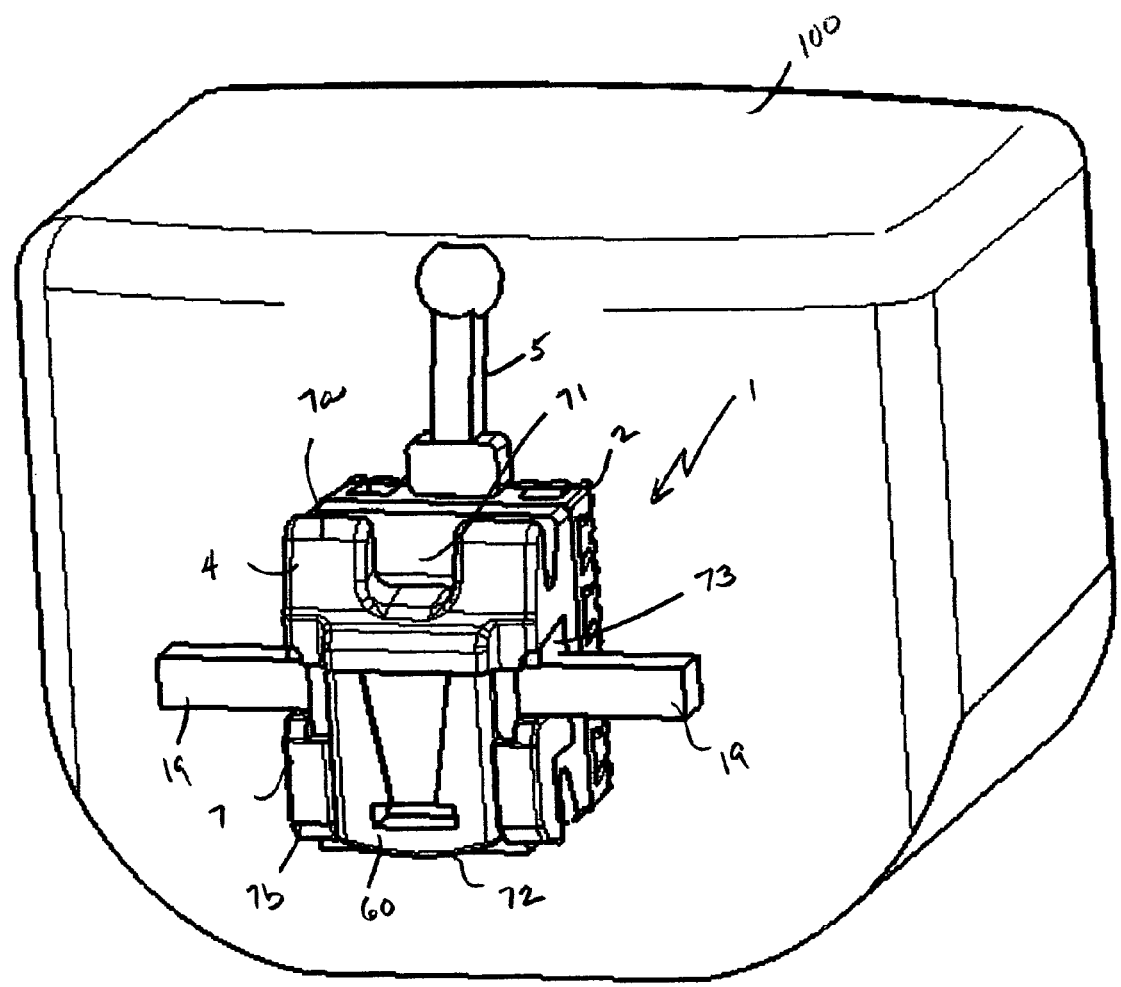
FIG. 11 is a perspective view of FIG. 9 fully assembled on a patient's tooth.
Figure 12:
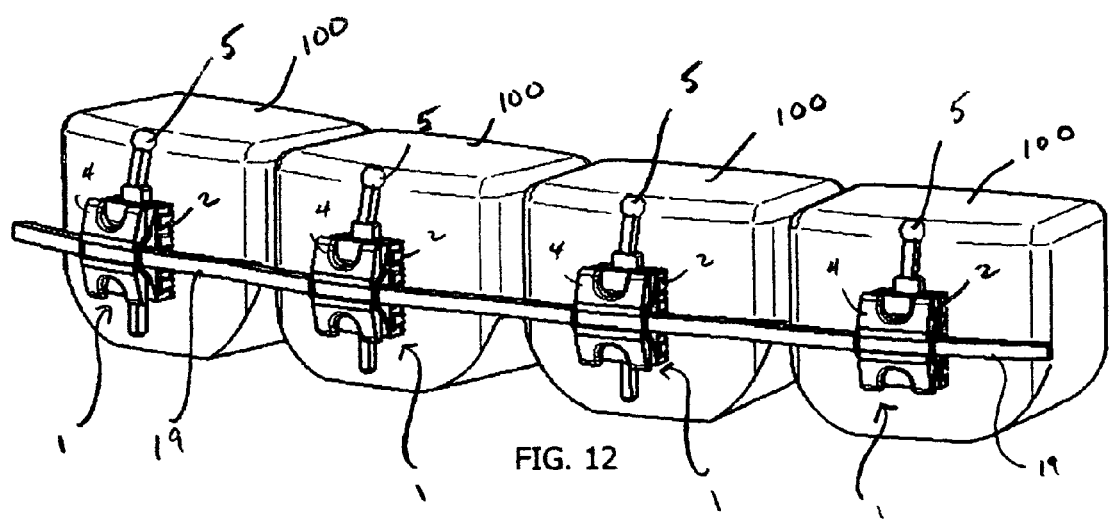
FIG. 12 is a perspective view of system of the present invention fully assembled on a patient's teeth.

FIGS. 10-12 depict another embodiment of the present invention wherein the orthodontic device 7 has a door 60 for enclosing the central cavity 73 to thereby lock the wire 19 into place. The orthodontic device 7 comprises at least two u-shaped protrusions, 71 and 72 respectively, on opposing ends 7a and 7b respectively; and a central cavity 73 for receiving a wire 19. The orthodontic device 7 is attached to the connecting plate 4 which is secured to the base plate 2 with the pin 5. FIGS. 11-12 shows the apparatus 1 assembled onto a patient's teeth 100.

Figure 13:
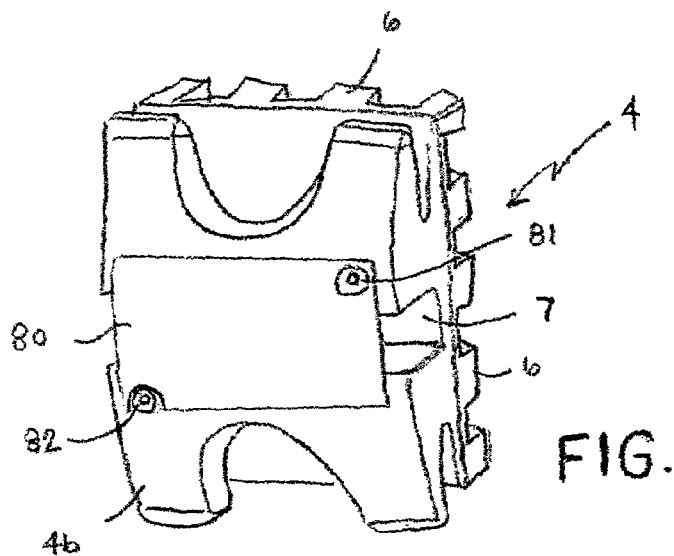
FIG. 13 is a perspective view of the self-ligating bracket of the present invention in a closed position.
Figure 14:
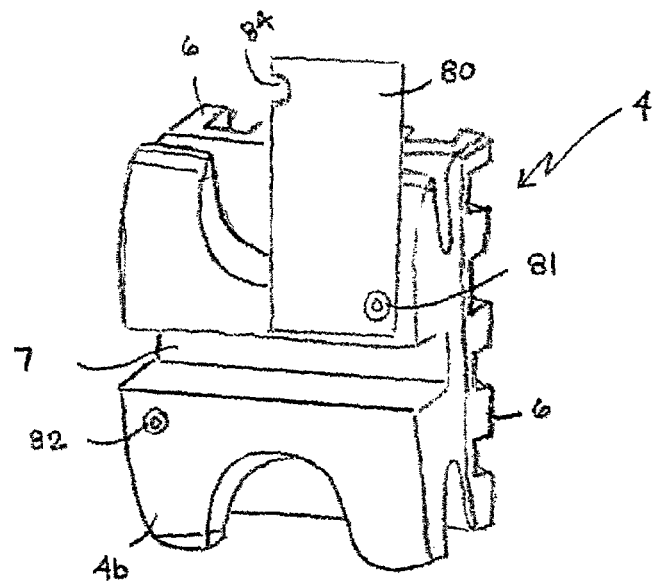
FIG. 14 is a perspective view of the self-ligating bracket of the present invention in an opened position.
Figure 15:
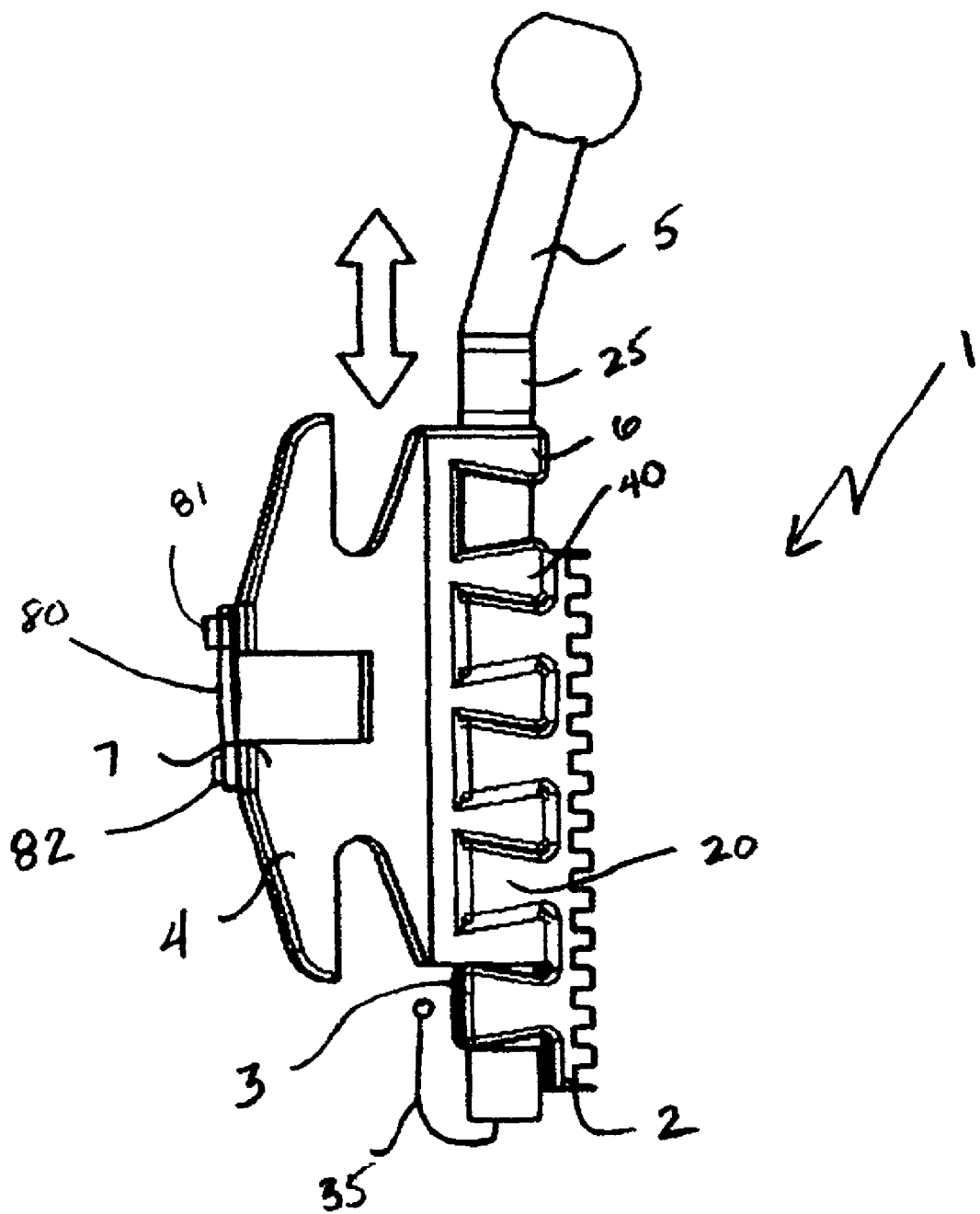
FIG. 15 is a side view of the self ligating bracket system of the present invention.
Figure 16:
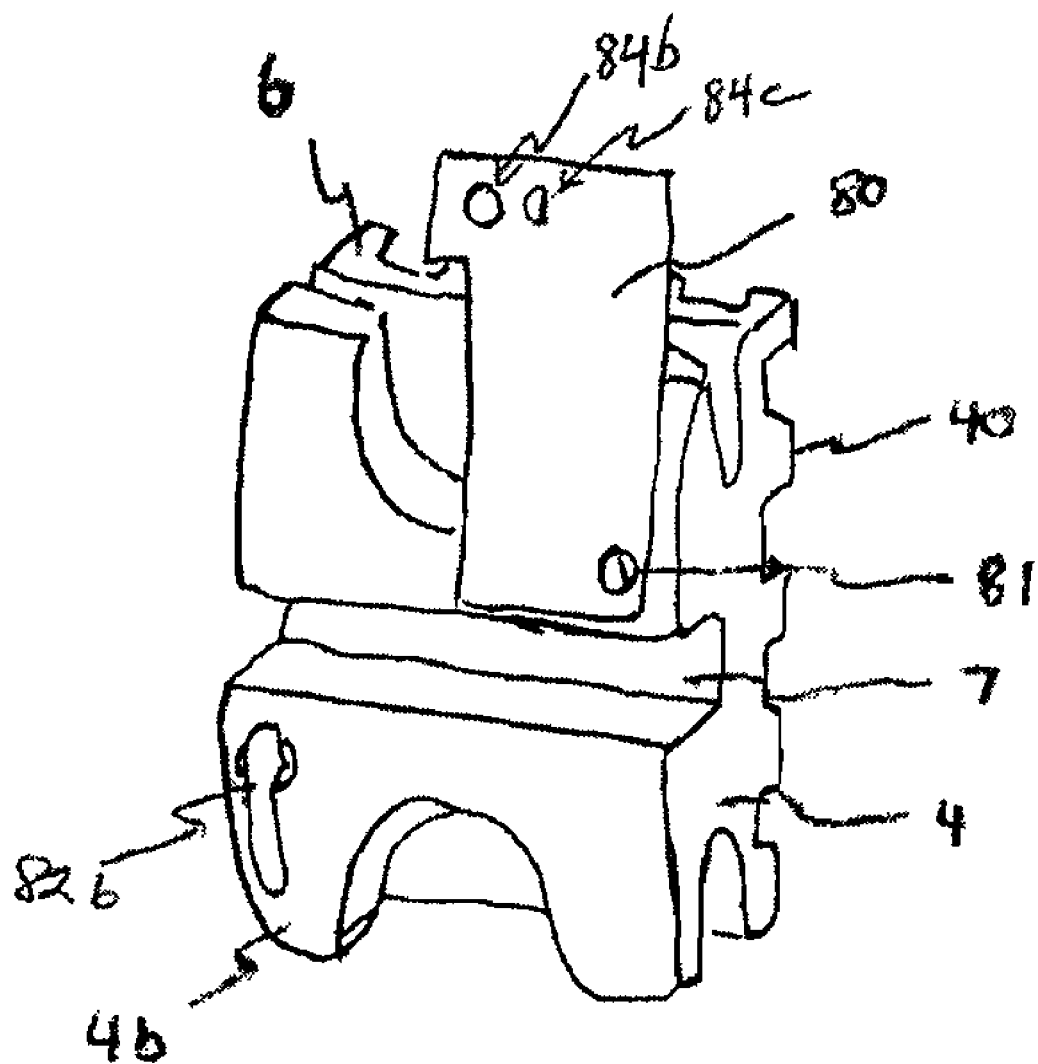
FIG. 16 is a front perspective view of the self ligating bracket and locking pin in an open position.
Figure 17:
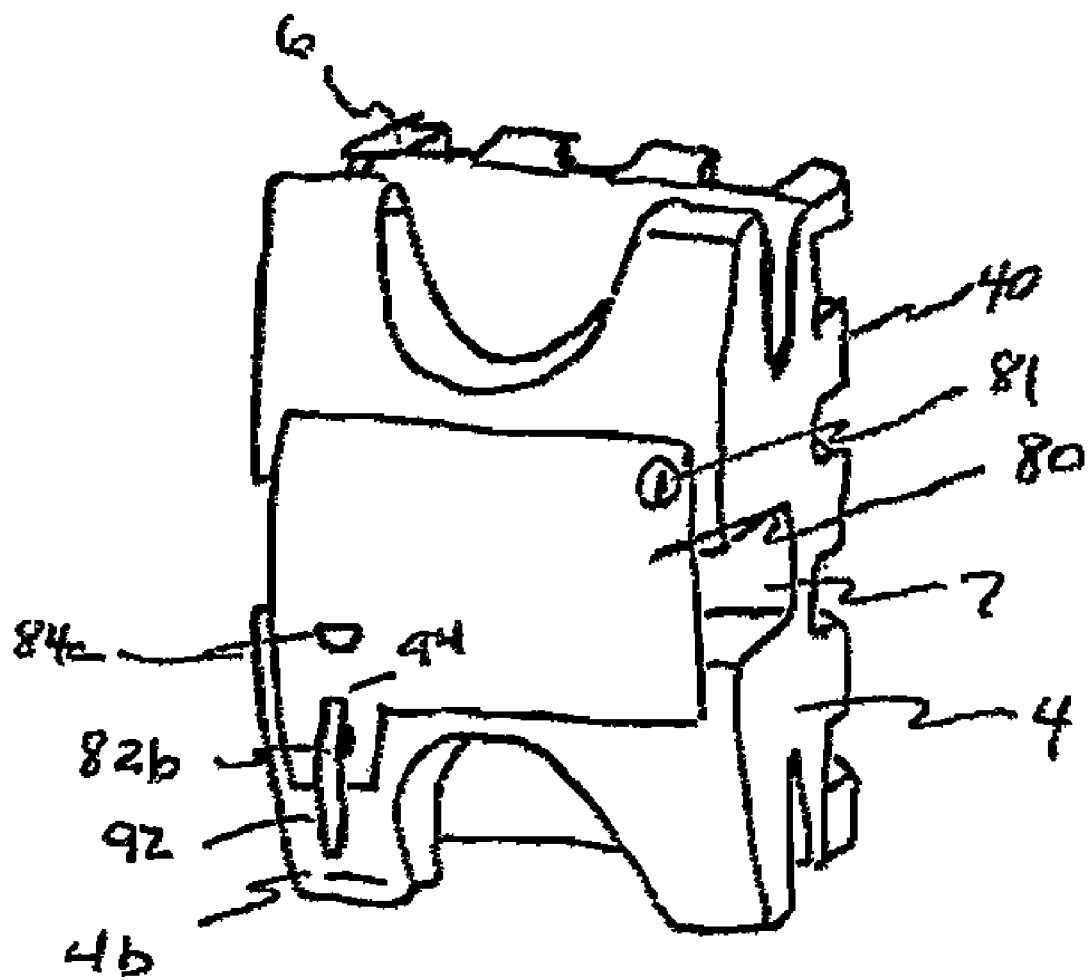
FIG. 17 is a front perspective view of the self ligating bracket and locking pin in a closed position.
Figure 18:
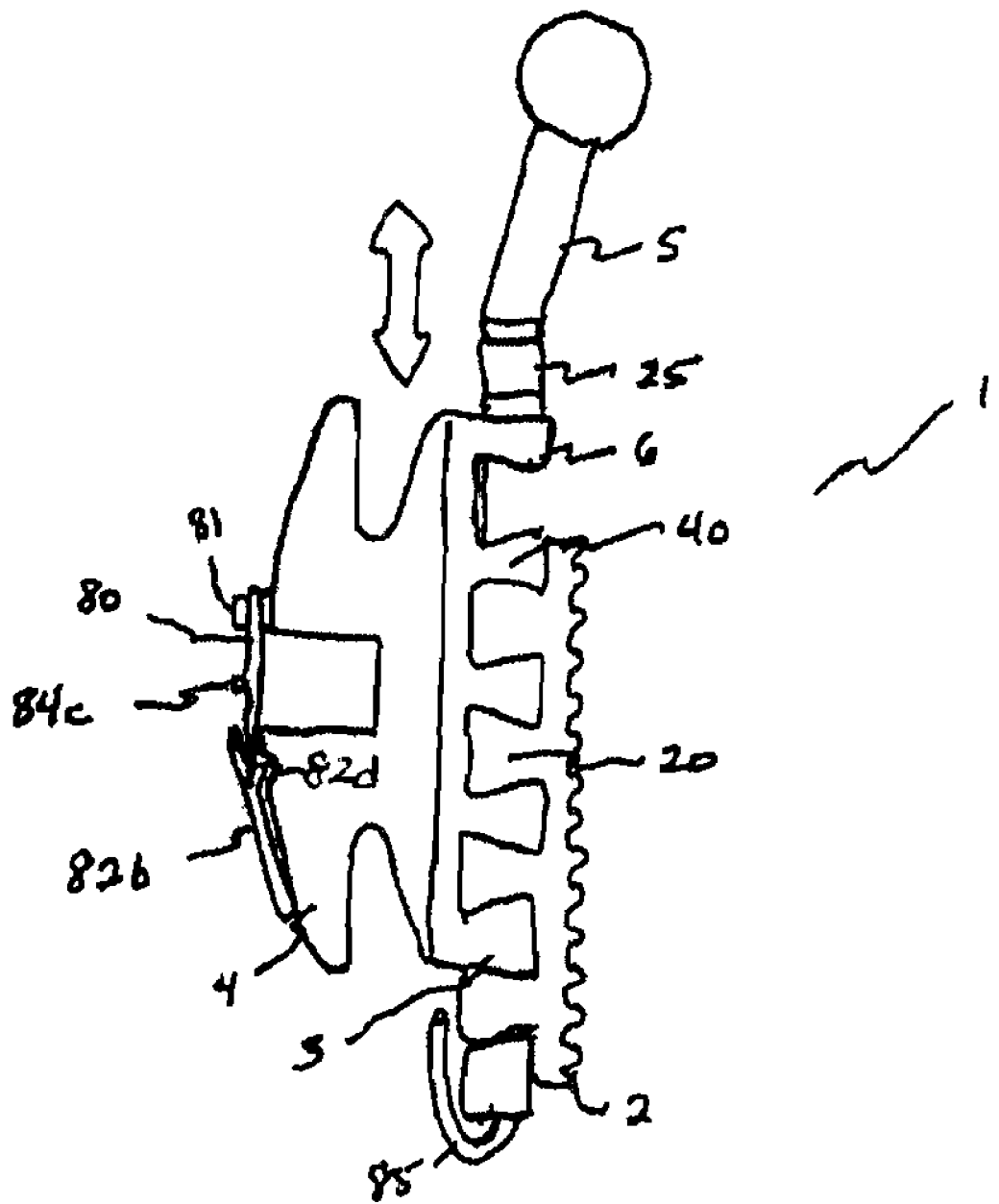
FIG. 18 is a side view of self ligating bracket with locking system.
Figure 19:
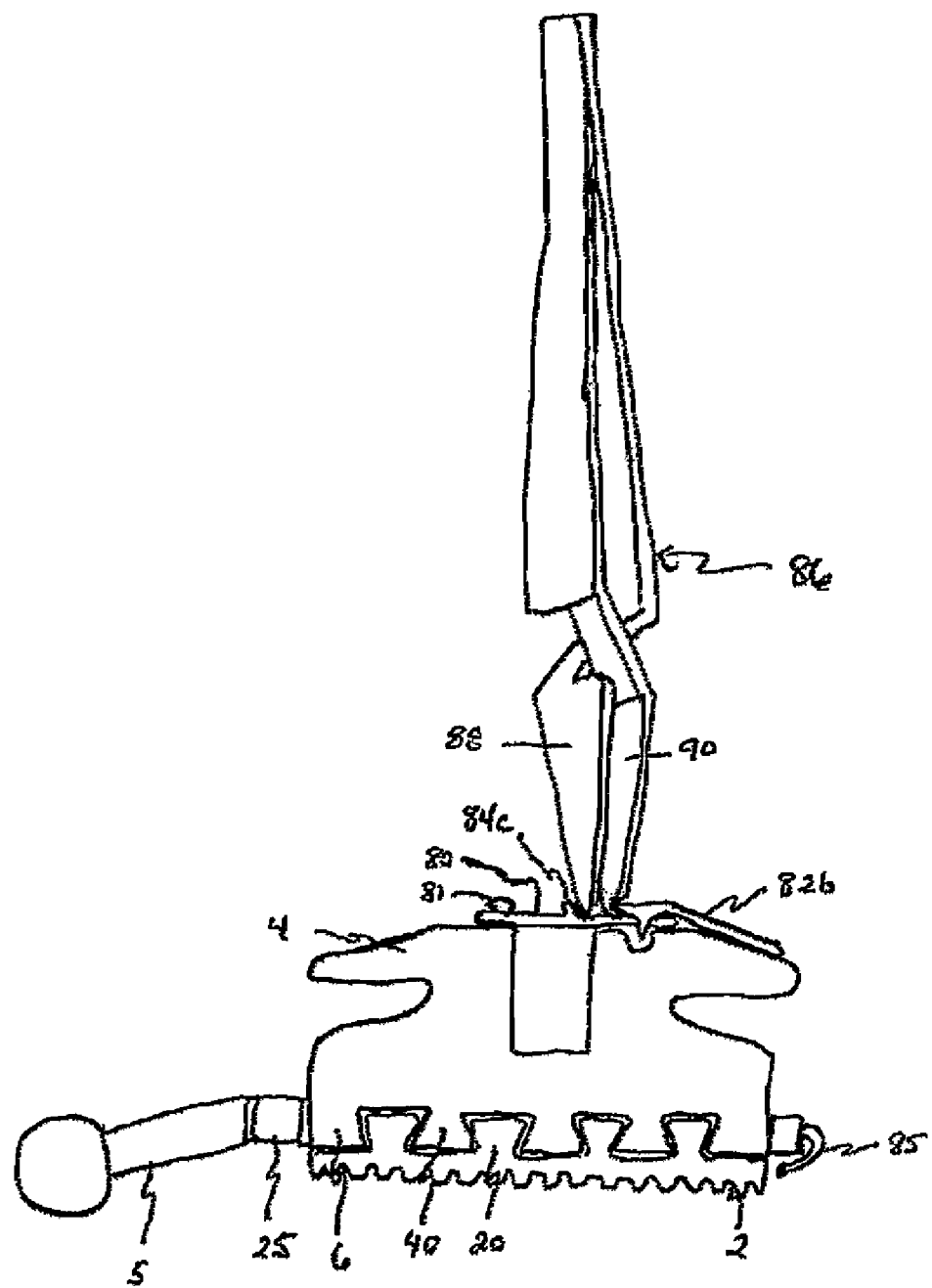
FIG. 19 is a side view of self ligating bracket with locking system showing a tweezers device in use.

Referring now to FIGS. 13-15, the present invention provides for a bracket housing or connecting plate 4 comprising at least two opposing sides, a rear side being a tooth engaging side and a front side 4b having a cavity 7 for receiving a wire (not shown); and a cover plate 80 pivotally attached to the front side 4b of said bracket housing 4, the cover plate 80 is designed to be moveable from an open to a closed position to secure and hold the wire within the cavity 7 of said front side 4b of the bracket housing 4.

The front side 4b of the bracket housing 4 comprises a protrusion 82. The cover plate 80 comprises an indentation 84 for receiving the protrusion 82 during the closed position. The cover plate 80 is attached to a pivot point 81 attached to the front side 4b of the bracket housing 4.

The cover plate 80 is moved in a downward direction to the closed position when the bracket is placed on a lower tooth of patient's mouth and the cover plate 80 is moved in an upward direction to the closed position when the bracket is placed on an upper tooth of patient's mouth. In all other respects, the connecting plate is as described above.

FIGS. 16-19 depict another embodiment of a bracket housing or connecting plate 4 of the present invention showing a cover plate 80 pivotally attached to the front side 4b of a bracket in both the open and closed position. The cover plate 80 is designed to be movable from an open to a closed position to secure and hold the wire within the cavity 7 of said front side 4b of the bracket housing 4.

The front side 4b of the bracket housing 4 comprises a cover plate locking device first member, for example, spring clip 82b. The cover plate 80 comprises a cover plate locking device second member, for example, an opening 84b for receiving the spring clip 82b during the closed position. A ridge 84c is located just above the opening 84b and is used to engage an opening tool 86, for example, a tweezers, for unlocking the cover plate 80 from the closed position. In a preferred embodiment, spring clip 82b comprises a first end 92 being attached to the bracket housing 4 and a second end 94 having a protrusion 82d for engaging the aperture 84b of the cover plate 80 during the locked position.

The cover plate 80 is moved in a downward direction to the closed position when the bracket is placed on a lower tooth of a patient's mouth and the cover plate 80 is moved in an upward direction to the closed position when the bracket is placed on an upper tooth of a patient's mouth.

As the cover plate 80 is moved into the closed position, spring clip 82b is displaced from bracket housing 4b as cover plate 80 slides under spring clip 82b. Upon cover plate 80 reaching it fully closed position, spring clip 82b engages opening 84b to lock cover plate 80 in its closed position. To open cover plate 80, opening tool 86 is used to apply opening forces to ridge 84c, thereby causing spring clip 82b to disengage from opening 84b and allowing cover plate 80 to move to its open position. Tool 86 comprises two legs, the first leg 88 contacts ridge 84c and the second leg 90 disengages the spring clip 82b from the aperture 84b of the cover plate 80.

Although the present invention has been described in connection with specific examples and embodiments, those skilled in the art will recognize that the present invention is capable of other variations and modifications within its scope. These examples and embodiments are intended as typical of, rather than in any way limiting on, the scope of the present invention as presented in the appended claims.

What is claimed is:

1. An adjustable orthodontic apparatus with a self ligating bracket and locking mechanism comprising:
 a base plate comprising opposing sides, a first side being a tooth engaging side and a second side comprising a first device for engaging and adjusting the vertical and horizontal position of a connecting plate;
 the connecting plate having opposing sides, a first side comprising a second device for engaging the second side of the base plate and allowing for the vertical and horizontal movement of the connecting plate as it relates to the base plate, a second side having an archwire channel for receiving an archwire;
 a securing device for locking the connecting plate to a desired position on the base plate;
 a cover plate pivotally attached to the connecting plate second side, the cover plate designed to be moveable by a single pivot point from an open position for allowing access to the archwire channel to a closed position for securing and holding the wire within the archwire channel, the cover plate comprising a locking element; and a locking device comprising a first end attached to the connecting plate second side and a second end for engaging the locking element during a cover plate locked position; wherein the first device and the second device each comprise at least four protrusions, at least one of the protrusions of the first device having a geometric shape that creates a retentive undercut with an opposing geometric shape of at least one of the protrusions of the second device to form the mechanical engagement.

2. The apparatus of claim 1 wherein the archwire channel is contained within a bracket housing, the cover plate is pivoted towards and covers the archwire channel during the closed position, the locking element is an aperture, and the locking device comprises a pin having opposing ends, a first end being attached to the bracket housing and a second end having a pin protrusion for engaging the aperture of the cover plate during the locked position.

3. The bracket assembly of claim 2 wherein the locking device comprises a spring and the cover plate further comprises an elevated ridge situated adjacent the aperture.

4. The apparatus of claim 2 wherein the first device of the second side of the base plate comprises at least two vertically positioned protrusions and at least two horizontally positioned protrusions and the second device of the first side of the connecting plate comprises at least two vertically positioned protrusions and at least two horizontally positioned protrusions.

5. The apparatus of claim 4 wherein there are a plurality of spaces in between each of the protrusions in the second side of the base plate and the first side of the connecting plate, the plurality of spaces provides for a protrusion channel for the protrusions to move during adjustment of the connecting plate relative to the base plate, and the securing device is situated within the protrusion channel when the connecting plate is locked onto the base plate.

6. The apparatus of claim 2 wherein the first device of the second side of the base plate comprises a plurality of vertical and horizontal column of protrusions and the second device of the first side of the connecting plate comprises a plurality of vertical and horizontal column of protrusions, the plurality of column of protrusions provides for a plurality of vertical and horizontal protrusion channels.

7. The apparatus of claim 6 wherein the protrusion channels provides the protrusions to move during adjustment of the connecting plate relative to the base plate, the protrusions are designed to move within the channels during the adjustment of the connecting plate relative to the base plate, and the securing device is situated within a protrusion channel when the connecting plate is locked into a certain position relative to the base plate.

8. The apparatus of claim 6 wherein at least one of the protrusions of the connecting plate and at least one of the protrusions of the base plate engage one another when the securing device locks the connecting plate to the base plate.

9. The bracket assembly of claim 1 wherein the archwire channel forms a first and second opposing portion, the cover plate pivotally attaches to the first opposing portion and the locking device attaches to the second opposing portion.

10. The adjustable orthodontic apparatus of claim 1 wherein the first device mechanically engages and is freely movable within the second device and the second device mechanically engages and is freely movable within the first device while the base plate and the connecting plate are engaged, such that separation of the base plate and connecting plate can occur during an adjustment phase.

11. An adjustable orthodontic system with self ligating brackets and locking device comprising:

a plurality of self ligating brackets, each bracket comprising:

a base plate comprising opposing sides, a first side being a tooth engaging side and a second side comprising a first device for engaging and adjusting the vertical and horizontal position of a connecting plate;

the connecting plate having opposing sides, a first side comprising a second device for engaging the second side of the base plate and allowing for the vertical and horizontal movement of the connecting plate as it relates to the base plate, a second side having an archwire channel for receiving an archwire;

a securing device for locking the connecting plate to a desired position on the base plate;

a cover plate pivotally attached to the connecting plate second side, the cover plate designed to be moveable by a single pivot point from an open position for allowing access to the archwire channel to a closed position for securing and holding the wire within the channel, the cover plate comprising a locking element and a disengagement element; and a locking device comprising a first end attached to the connecting plate second side and a second end for engaging the locking element during a cover plate locked position;

a wire for engagement within the archwire channel; and a tool for opening and closing the cover plate; wherein the first device and the second device each comprise at least four protrusions, at least one of the protrusions of the first device having a geometric shape that creates a retentive undercut with an opposing geometric shape of at least one of the protrusions of the second device to form the mechanical engagement.

12. The system of claim 11 wherein the archwire channel is contained within a bracket housing, the cover plate is pivoted towards and covers the archwire channel during the closed position, the locking element is an aperture, and the locking device comprises a pin having opposing ends, a first end being attached to the bracket housing and a second end having a pin protrusion for engaging the aperture of the cover plate during the locked position.

13. The system of claim 12 wherein the tool comprises at least two legs, the first leg designed to contact the disengagement element and the second leg designed to disengage the pin protrusion from the aperture of the cover plate.

14. The system of claim 12 wherein the archwire channel forms a first and second opposing portion, the cover plate pivotally attaches to the first opposing portion and the locking device attaches to the second opposing portion.

15. The system of claim 12 wherein the locking device comprises a spring and the cover plate further comprises an elevated ridge situated adjacent the aperture.

16. The system of claim 12 wherein the first device of the second side of the base plate comprises at least two vertically positioned protrusions and at least two horizontally positioned protrusions and the second device of the first side of the connecting plate comprises at least two vertically positioned protrusions and at least two horizontally positioned protrusions.

17. The system of claim 16 wherein there are a plurality of spaces in between each of the protrusions in the second side of the base plate and the first side of the connecting plate; the plurality of spaces provides for a protrusion channel for the protrusions to move during adjustment of the connecting plate relative to the base plate; and the securing device is situated within the protrusion channel when the connecting plate is locked onto the base plate.

18. The system of claim 12 wherein the first device of the second side of the base plate comprises a plurality of vertical and horizontal column of protrusions and the second device of the first side of the connecting plate comprises a plurality of vertical and horizontal column of protrusions, the plurality of column of protrusions provides for a plurality of vertical and horizontal protrusion channels.

19. The system of claim 18 wherein the protrusion channels provides the protrusions to move during adjustment of the connecting plate relative to the base plate, the protrusions are designed to move within the protrusion channels during the adjustment of the connecting plate relative to the base plate, and the securing device is situated within a protrusion channel when the connecting plate is locked into a certain position relative to the base plate.

20. The system of claim 18 wherein at least one of the protrusions of the connecting plate and at least one of the protrusions of the base plate engage one another when the securing device locks the connecting plate to the base plate.

21. The system of claim 11 wherein the first device mechanically engages and is freely movable within the second device and the second device mechanically engages and is freely movable within the first device while the base plate and the connecting plate are engaged, such that separation of the base plate and connecting plate can occur during an adjustment phase.

* * * * *